US011865215B2

(12) United States Patent
Fradera Gelabert et al.

(10) Patent No.: US 11,865,215 B2
(45) Date of Patent: Jan. 9, 2024

(54) TABLET COMPOSITIONS COMPRISING ABIRATERONE ACETATE

(71) Applicant: SYNTHON B.V., Nijmegen (NL)

(72) Inventors: Sara Fradera Gelabert, Sant Boi de Llobregat (ES); Manuel Gago Guillan, Sant Boi de Llobregat (ES); Lisardo Alvarez Fernandez, Sant Boi de Llobregat (ES); Rohit Kumar, Sant Boi de Llobregat (ES)

(73) Assignee: Synthon B.V., Nijmegen (NL)

( * ) Notice: Subject to any disclaimer, the term of this patent is extended or adjusted under 35 U.S.C. 154(b) by 525 days.

(21) Appl. No.: 17/044,698

(22) PCT Filed: Jan. 25, 2019

(86) PCT No.: PCT/EP2019/051921
§ 371 (c)(1),
(2) Date: Oct. 1, 2020

(87) PCT Pub. No.: WO2019/206472
PCT Pub. Date: Oct. 31, 2019

(65) Prior Publication Data
US 2021/0038525 A1 Feb. 11, 2021

(30) Foreign Application Priority Data

Apr. 26, 2018 (EP) .................... 18169623

(51) Int. Cl.
A61K 9/28 (2006.01)
A61K 9/20 (2006.01)
A61K 31/58 (2006.01)

(52) U.S. Cl.
CPC ............ A61K 9/2893 (2013.01); A61K 9/205 (2013.01); A61K 9/2009 (2013.01); A61K 9/2013 (2013.01); A61K 9/2072 (2013.01); A61K 9/2095 (2013.01); A61K 31/58 (2013.01)

(58) Field of Classification Search
CPC .. A61K 9/2893; A61K 9/2009; A61K 9/2013; A61K 9/205; A61K 9/2072; A61K 9/2095; A61K 31/58; A61P 13/08; A61P 35/00
See application file for complete search history.

(56) References Cited

U.S. PATENT DOCUMENTS

2015/0246060 A1   9/2015 Murphy et al.

FOREIGN PATENT DOCUMENTS

| CN | 102336801 | 2/2012 |
| CN | 102743393 | 10/2012 |
| WO | WO 93/20097 | 10/1993 |
| WO | WO2015/032873 | 3/2015 |
| WO | WO2015/114314 | 8/2015 |
| WO | WO2017/209939 | 12/2017 |

OTHER PUBLICATIONS

Ministry of Health of the Russian Federation, SmPC—Summary of Product Characteristics, ZYTIGA 500mg of Nov. 15, 2016 (including English translation).
Ministry of Health of the Russian Federation, SmPC—Summary of Product Characteristics, Amendment No. 1 of Dec. 12, 2017 (including English translation).
EMA Assessment report Zytiga of Sep. 15, 2016.
Excerpt from the Russian regulatory database listing Zytiga (including English translation), Dec. 12, 2017.
Third Party Observations regarding EP 19 70 1132.3, Publication No. EP3784218, Sep. 2021.

Primary Examiner — Aradhana Sasan
(74) Attorney, Agent, or Firm — Buscher Patent PLLC

(57) ABSTRACT

The present invention relates to a tablet composition for oral administration of abiraterone acetate, particularly to pharmaceutical granulates and tablets giving immediate release of abiraterone acetate in the stomach.

20 Claims, 1 Drawing Sheet

Dissolution profiles of formulations 1 and 2 of abiraterone acetate film-coated tablets compared to Zytiga 500 mg
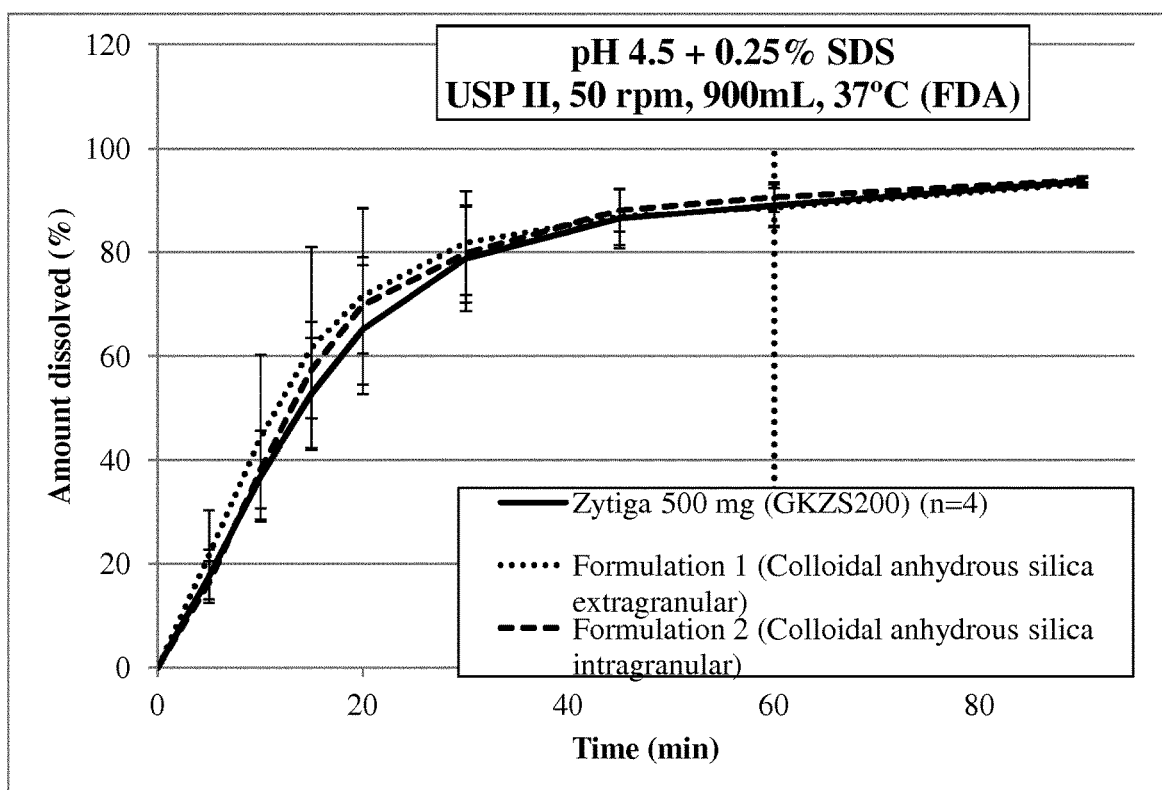

TABLET COMPOSITIONS COMPRISING ABIRATERONE ACETATE

BACKGROUND OF THE PRESENT INVENTION

Abiraterone acetate (3β-acetoxy-17-(3-pyridyl)androsta-5,16-diene) of formula (1),

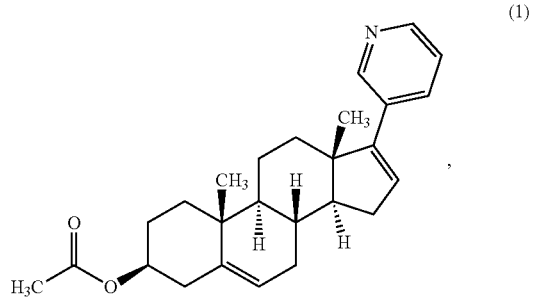

is a pharmaceutically active compound used for treatment of castration-resistant prostate cancer in adult men, together with a low dose of prednisone or prednisolone.

Abiraterone acetate itself is a prodrug. It is converted in vivo by hydrolysis of the 3-acetyl group to abiraterone, an androgen biosynthesis inhibitor. Specifically, abiraterone selectively inhibits the enzyme CYP 17, which is required for androgen biosynthesis in testicular, adrenal and prostatic tumour tissues.

Abiraterone acetate is marketed in a tablet form under the brand name Zytiga. One tablet comprises 250 mg or 500 mg of the active substance. The 250 mg tablet further comprises microcrystalline cellulose (MCC), sodium croscarmellose, lactose monohydrate (corresponding to 189 mg of lactose), povidone (K29/K32), sodium lauryl sulfate, magnesium stearate and colloidal anhydrous silica. The total weight of a single tablet is about 715 mg, making the overall content of the abiraterone acetate in the tablet about 35% w/w. The 500 mg tablet includes excipients not used in the 250 mg; hypromellose, silicified microcrystalline cellulose and coating powder Opadry Purple. Silicified microcrystalline cellulose is more expensive than normal MCC.

The approved method of administration is 1000 mg (four tablets) in a single daily dose that must not be taken with food (it should be taken at least two hours after eating and no food should be eaten for at least one hour after taking the tablets). Tablets must be swallowed whole, with water. Taking the tablet with food significantly and undesirably increases the absorption of abiraterone acetate. Following the oral administration in the fasting state, the time to reach maximum plasma concentration of abiraterone is approx. 2 hours.

Abiraterone acetate was first disclosed in WO 93/20097. Abiraterone is highly insoluble in water (less than 0.1 mg/ml). As a result, abiraterone acetate is pharmacologically considered in the BCS System as a Class IV compound, i.e. a compound of low solubility and low permeability.

No specific patent application specifically deals with the commercially available abiraterone acetate tablets Zytiga®. The available information published at the publication of the marketing authorization approvals teaches that the tablet is made by a wet granulation, but no details were disclosed. CN 102743393 discloses tablet compositions having the same qualitative composition and the same concentration of abiraterone acetate in the tablet as in the Zytiga tablet. Little is known about the method how to make such tablet.

CN102336801 discloses a tablet comprising a high load of abiraterone acetate, however this composition exhibits a slower dissolution profile when comparing to the approved Zytiga 250 mg tablet.

WO2015032873 discloses a tablet comprising a high load of abiraterone acetate of 50 to 80% w/w and one wetting agent. However these compositions have low bioavaility when comparing to the approved Zytiga 250 mg tablet, probably this is due to the high percentage of abiraterone present.

There is still need of finding an additional oral formulation of abiraterone high load which overcome the problems of the prior art and is bioequivalent to the commercial abiraterone tablet Zytiga® 500 mg.

BRIEF DESCRIPTION OF THE DRAWING

FIG. 1 depicts the in vitro dissolution profiles of the compositions of Example 1 as compared to the commercially available tablet.

DETAILED DESCRIPTION OF THE PRESENT INVENTION

The present invention relates to a immediate release pharmaceutical composition, advantageously a tablet, of abiraterone acetate comprising an abiraterone acetate granulate. The term "immediate release" as used throughout the disclosure and claims means, in accordance with common understanding, that more than 70% of the dose of the active pharmaceutical ingredient is released in the stomach within less than 30 minutes after oral administration.

Abiraterone acetate of formula (1) above is a known compound, which is commercially available or may be produced by procedures known in the art. Abiraterone acetate, as used throughout the present invention, comprises any solid state form thereof, including any crystalline polymorphic form thereof. The potential differences in inherent solubility of the respective polymorphs do not have any influence on the dissolution rate of abiraterone acetate composition.

One embodiment of the present invention relates to a tablet composition comprising granules and one or more extragranular pharmaceutical excipients, wherein the granules comprise:

a) Abiraterone acetate in an amount of from 40% to 60% by weight based on the total weight of the composition;

b) Colloidal anhydrous silica in an amount of from 0.1% to 5% by weight based on the total weight of the composition;

c) surfactant in an amount of from 0.1% to 5.5%, preferably from 0.3 to 3% by weight based on the total weight of the composition;

and wherein the extragranular excipients comprise surfactant in an amount of from 0.5% to 7%, preferably from 3% to 6% by weight based on the total weight of the composition.

These tablet compositions of abiraterone acetate are suitable for oral administration of abiraterone acetate to humans comprising up to 1000 mg of the active substance in a single dose.

The granulate of the present invention comprises abiraterone acetate in an amount from 40% to 60%, preferably 42% to 50%, even more preferably 43% to 48% by weight based on the total weight of the composition.

The preferred way to formulate abiraterone acetate is wet granulation, however when the formulations of the commercial product are wet granulated the yield of the process is low because of sticking to the equipment walls and filters and the poor flowability of the intragranular raw materials (mainly abiraterone acetate).

It was found by the present inventors that a tablet composition comprising abiraterone acetate, colloidal anhydrous silica intragranularly and surfactant intragranularly and extragranularly in the amounts described above reduces the sticking and improves the flow properties of the formulation.

The granulate of the present invention comprises surfactant.

Surfactants are compounds that lower the surface tension (or interfacial tension) between two liquids, between a gas and a liquid, or between a liquid and a solid. Surfactants may act as wetting agents. Wetting agent is a surfactant that, when dissolved in water, lowers the advancing contact angle, aids in displacing an air phase at the surface, and replaces it with a liquid phase. A preferred surfactant to be used according to the present invention is sodium lauryl sulphate, polysorbate 80, poloxamer, most preferably sodium lauryl sulphate. Surfactants in accordance with the present invention, are preferably used intragranularly in an amount of from 0.1% to 5.5% preferably 0.3% to 3%, more preferably 0.2% to 2%, most preferably 0.3% to 1% by weight based on the total weight of the composition.

Glidants enhance product flow by reducing interparticulate friction. A suitable example is colloidal silicon dioxide (colloidal anhydrous silica), starch or talc.

The granulate of the present invention contains colloidal anhydrous silica, this excipient is widely used as a glidant. Its small particle size and large specific surface area gives it desirable flow characteristics that are exploited to improve the flow properties of dry powders in a number of processes such as tabletting and capsule filling. Colloidal anhydrous silica is normally added as extragranular excipient. Nevertheless, in the present invention this excipient has been added as intragranular component. Colloidal anhydrous silica in accordance with the present invention is preferably used intragranularly in an amount of from 0.1% to 5%, preferably 0.3% to 3%, more preferably 0.5% to 1% by weight based on the total weight of the composition.

The flowability of the powders is governed by forces between individual powder particles. A number of different forces determine the mechanism of adhesion: van-der-Waals forces, electrostatic forces, liquid bridges and entanglement. Typically, the smaller the solid particles are, the more pronounced these effects are, and consequently the more cohesive the powder and poor flow properties. Colloidal anhydrous silica helps to improve the flow of powders by acting to counteract these different mechanisms. Van-der-Waals forces and electrostatic attraction decrease with increasing distance between the particles. Small colloidal anhydrous silica aggregates adhere to the surface of the larger powder particles, thereby increasing the distance, and reducing the attractive forces between them. The addition of the intragranular colloidal anhydrous silica improves the flow of the granule.

Further, the granulate of the present invention can comprise other pharmaceutical acceptable excipients, chosen from, for example, diluents, binders, disintegrants.

Diluents are fillers which are used to increase the bulk volume of a tablet or capsule. By combining a diluent with the active pharmaceutical ingredient, the final product is given adequate weight and size to assist in production and handling. Binders hold the excipients that are present in a tablet together. Binders ensure that tablets and granules can be formed having the desired or required mechanical strength.

The granulate of the present invention preferably contains at least one diluent and at least one binder.

Diluents are preferably used intragranularly in an amount of from 10 to 30% by weight based on the total weight of the composition. Suitable examples of diluents to be used in accordance with the present invention include starch, pregelatinized starch, microcrystalline cellulose, and calcium phosphate. Lactose, sorbitol, mannitol and sucrose are also suitable water-soluble diluents.

In a preferred embodiment of the present invention, the diluents to be used are lactose monohydrate, microcrystalline cellulose or mixtures thereof.

Binders which are suitable for use in accordance with the present invention include povidone, hydroxypropyl methylcellulose, dihydroxy propylcellulose, and sodium carboxyl methylcellulose. Binders are preferably used intragranularly in an amount of from 1% to 5% by weight based on the total weight of the composition. A preferred binder is hydroxypropyl methylcellulose (hypromellose).

The granules of the present invention may also contain a disintegrant. Disintegrants are added to a tablet composition extragranularly to promote the breakup of the tablet into smaller fragments and intragranularly to promote the breakup of the granules that contain Abiraterone. Suitable examples of disintegrants to be used in accordance with the present invention include crospovidone, sodium starch glycolate, croscarmellose sodium, and mixtures of any of the foregoing. A preferred disintegrant is croscarmellose sodium. Disintegrants in accordance with the present invention, are preferably used intragranularly in an amount of from 0.5% to 8% by weight, preferably from 1% to 6%, more preferably from 2% to 5% by weight based on the total weight of the composition In the tablet composition, the extragranular excipients comprise at least one surfactant. The surfactant may be the same or different than that as used in the granulate composition.

A preferred surfactant to be used according to the present invention is sodium lauryl sulphate, polysorbate 80, poloxamer, most preferably sodium lauryl sulphate. Surfactants are preferably used extragranularly in an amount of from 0.5% to 7%, preferably 3% to 6%, by weight based on the total weight of the composition.

The combination of intragranular silica and surfactant intragranular and extragranular results in a bioequivalent product to Zitiga® with excellent flow properties.

Other suitable extragranular pharmaceutical excipients in a tablet composition include, without limitation: disintegrants, diluents. The disintegrant and diluents may be the same or different than that as used in the granulate composition. In a preferred embodiment diluents are used extragranularly in an amount of from 10% to 30%, preferably 15% to 20%, by weight based on the total weight of the composition. A preferred diluent to be used is MCC. One of the advantages of the present invention is that it enables the use of the conventional MCC instead of the MCC silicified which is more expensive.

In a preferred embodiment disintegrants are used extragranularly in an amount of from 1% to 8%, preferably 4% to 6%, by weight based on the total weight of the composition.

The tablet composition of the invention may also contain a lubricant. Lubricants are generally used in order to reduce sliding friction. In particular, to decrease friction at the interface between a tablet's surface and the die wall during ejection, and reduce wear on punches and dies. Suitable lubricants to be used in accordance with the present invention include magnesium stearate, calcium stearate, stearic acid, glyceryl behenate, hydrogenated vegetable oil, and glycerine fumarate.

Lubricants preferably are used in a total amount of from 0.05% to 5% by weight based on the total weight of the composition.

In a preferred embodiment, the tablet composition of the present invention contains the following ingredients, based on the total weight of the composition:
1. Granules comprising intragranularly:
    a) Abiraterone acetate in an amount of from 40% to 60% by weight based on the total weight of the composition;
    b) Colloidal anhydrous silica in an amount of from 0.1% to 5% by weight based on the total weight of the composition;
    c) Surfactant in an amount of from 0.1% to 3% by weight based on the total weight of the composition;
    d) Disintegrant in an amount of from 1% to 8% by weight based on the total weight of the composition;
    e) Binder in an amount of from 1% to 5% by weight based on the total weight of the composition; and
    f) Diluent(s) in an amount of from 10% to 30% by weight based on the total weight of the composition.
2. Extragranular excipients comprising:
    a) Surfactant in an amount of from 3% to 7% by weight based on the total weight of the composition;
    b) Disintegrant in an amount of from 1% to 8% by weight based on the total weight of the composition;
    c) Diluent(s) in an amount of from 10% to 30% by weight based on the total weight of the composition;
    d) Lubricant in an amount of from 0.05% to 5% by weight based on the total weight of the composition.

The tablet compositions described herein can be made using conventional methods and equipment well-known in the art. In a preferred embodiment the composition are prepared by granulation process. Granulation can be performed by a wet or dry process, wherein wet granulation using water or organic solvents or mixtures thereof as granulation liquid and dry granulation can be performed by processes known as slugging and/or roller compaction. Wet granulation with fluid bed is the preferred method of preparation.

In one embodiment of the present invention, the therapeutically effective dose of Abiraterone acetate is 500 mg.

The present invention further relates to a tablet composition as described hereinabove, prepared by a wet-granulation process, which process comprises:
a) Mixing abiraterone acetate and colloidal anhydrous silica, and optionally one or more pharmaceutically acceptable excipients to form a mixture;
b) Wet-granulating the resulting mixture with a solution, preferably a water solution, comprising surfactant;
c) Further mixing the obtained granulate with one or more further pharmaceutically acceptable excipients to form a further mixture, wherein the extragranular excipients comprise surfactant;
d) Compressing the mixture obtained in step (c) into a tablet; and optionally
e) Coating the tablet.

It is preferred that the abiraterone acetate is of low particle size, preferably of $D_{50}$ less than 20 microns, more preferably between 3-10 microns and/or $D_{90}$ less than 50 microns preferably between 10-25 microns. Granulates made from abiraterone acetate of higher particle size may negatively affect dissolution and or the hardness of final tablets. Accordingly, abiraterone acetate should be first milled and screened to the desirable particle size, if necessary, prior to charging in the granulator. The process of the present invention results in a higher yield.

The tablet compositions of the present invention show an in vitro dissolution profile wherein at least 70% of abiraterone acetate is released within thirty minutes when the composition is subjected to a dissolution study in 900 ml 0.25% SLS in 56.5 mM phosphate buffer, pH 4.5 using a USP apparatus II at 50 rpm at 37° C. The tablet composition in accordance with the present invention is bioequivalent in vitro and in vivo to the commercially available abiraterone acetate tablets.

FIG. 1 shows the in vitro dissolution profile of tablet compositions in accordance with the present invention as compared to commercially available tablets.

The present invention is illustrated by the following Examples.

EXAMPLES

Example 1

Two formulations of abiraterone acetate were prepared, formulation 2 was prepared according to the present invention and formulation 1 with the colloidal anhydrous silica extragranular.

TABLE 1

Pharmaceutical composition of formulation 1 and 2.

| Components | Formulation 1 mg/tablet | Formulation 1 % | Formulation 2 mg/tablet | Formulation 2 % |
|---|---|---|---|---|
| Uncoated tablets | | | | |
| Intragranular components | | | | |
| Abiraterone acetate | 500.00 | 44.64% | 500.00 | 44.64% |
| Lactose monohydrate | 253.20 | 22.61% | 253.20 | 22.61% |
| Croscarmellose sodium | 22.40 | 2.00% | 22.40 | 2.00% |
| Hypromellose 2910 15 mPa · s | 16.80 | 1.50% | 16.80 | 1.50% |
| Sodium lauril sulfate | 5.60 | 0.50% | 5.60 | 0.50% |
| Colloidal anhydrous silica | — | — | 8.40 | 0.75% |
| Extragranular components | | | | |
| Colloidal anhydrous silica | 8.40 | 0.75% | — | — |
| Microcrystalline cellulose | 184.80 | 16.50% | 184.80 | 16.50% |
| Croscarmellose sodium | 56.00 | 5.00% | 56.00 | 5.00% |
| Sodium laurilsulfate | 56.00 | 5.00% | 56.00 | 5.00% |
| Magnesium stearate | 16.80 | 1.50% | 16.80 | 1.50% |
| Tablet core weight | 1120.00 | 100.00% | 1120.00 | 100.00% |
| Coated tablets | | | | |
| Opadry II 85F purple | 33.60 | 3.00% | 33.60 | 3.00% |
| Total tablet weight | 1153.60 | 103.00% | 1153.60 | 103.00% |

The two formulations above were made according to the process depicted in the following scheme:

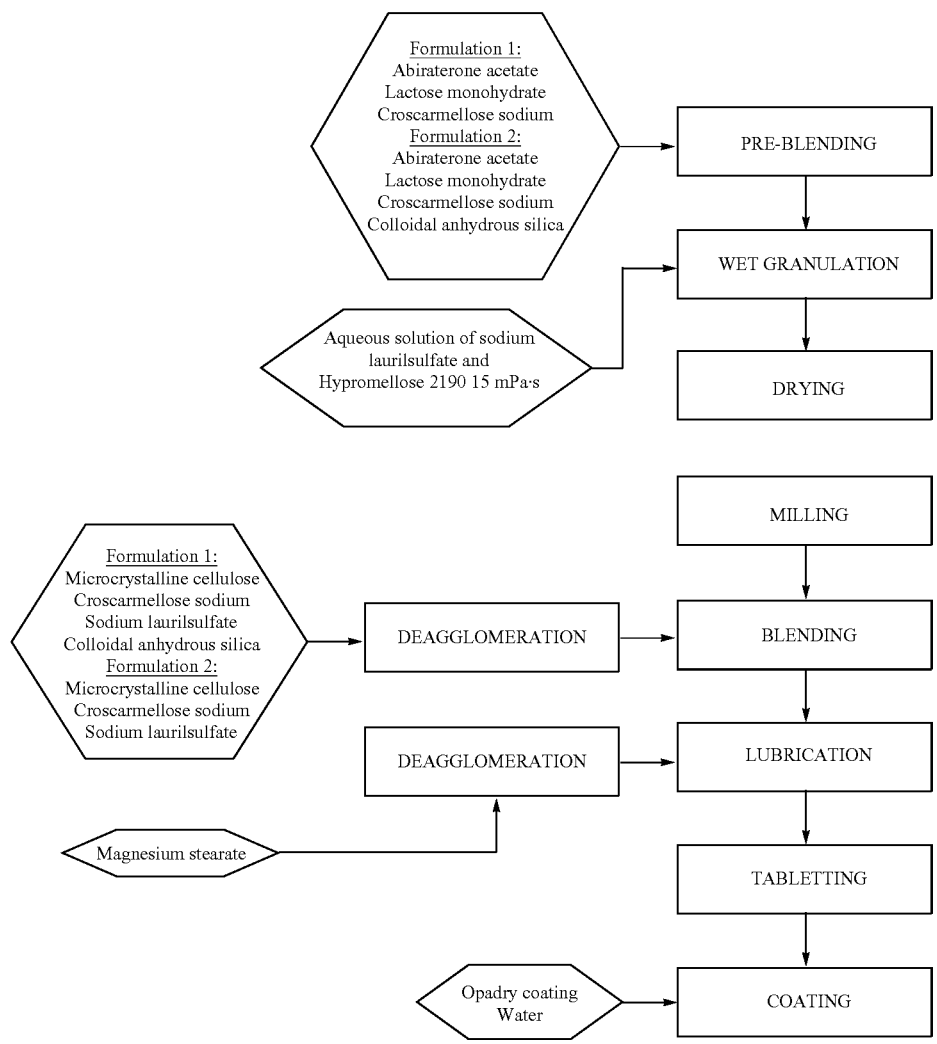

Table 2 compiles the granulation process yield, and granulate and final blend flow properties. The formulation of the present invention not only results in a wet granulation process with higher yield but also granulate and final blend flow are improved.

TABLE 2

Wet granulation process yield, granules and final blend flow properties.

| | | Formulation 1 | Formulation 2 |
|---|---|---|---|
| Wet granulation yield | | 87% | 98% |
| Granulate | Carr index | 29% | 18% |
| | Hausner Ratio | 1.40 | 1.23 |
| | Flow character* | Poor | Fair |
| Final blend | Carr index | 26% | 19% |
| | Hausner Ratio | 1.35 | 1.24 |
| | Flow character* | Poor | Fair |

*Powder flow character described in USP <1174>

Furthermore, the formulations of the present invention have similar dissolution profile to Zytiga 500 mg.

FIG. 1 shows the dissolution profiles of the tested formulation compared to Zytiga 500 mg. Both formulations showed similar dissolution profile to Zytiga 500 mg.

The invention claimed is:

1. A tablet composition comprising granules and one or more extragranular pharmaceutical excipients, wherein the granules comprise intragranularly:
   a) abiraterone acetate in an amount of from 40% to 60% by weight based on the total weight of the composition;
   b) colloidal anhydrous silica in an amount of from 0.1% to 5% by weight based on the total weight of the composition; and
   c) surfactant in an amount of from 0.1% to 3% by weight based on the total weight of the composition,
   wherein the extragranular excipients comprise surfactant in an amount of from 3% to 7% by weight based on the total weight of the composition, and a diluent in an amount from 10% to 30% by weight based on the total weight of the composition, wherein said diluent is microcrystalline cellulose (MCC).

2. The tablet composition according to claim 1, wherein the intragranular and extragranular surfactant is sodium lauryl sulphate.

3. The tablet composition according to claim 1, wherein the granule further comprises disintegrant intragranularly in an amount of from 1% to 8% by weight based on the total weight of the composition.

4. The tablet composition according to claim 3, wherein the disintegrant is croscarmellose sodium.

5. The tablet composition according to claim 1, wherein the granule further comprises binder intragranularly in an amount of from 1% to 5% by weight based on the total weight of the composition.

6. The tablet composition according to claim 5 wherein the binder is hypromellose.

7. The tablet composition according to claim 1, wherein the granule further comprises one or more diluents in an amount of from 10% to 30% by weight based on the total weight of the composition.

8. The tablet composition according to claim 7, wherein the diluent is lactose, microcrystalline cellulose (MCC) or a mixture of both.

9. The tablet composition according to claim 1, wherein the extragranular excipients further comprise one or more disintegrants in an amount from 1% to 8% by weight based on the total weight of the composition.

10. The tablet composition according to claim 1, wherein the extragranular excipients further comprise a lubricant in a total amount of from 0.05% to 5% by weight based on the total weight of the composition.

11. The tablet composition according to claim 1 prepared by a wet-granulation process, which process comprises
   a) mixing abiraterone acetate and colloidal anhydrous silica, and optionally one or more pharmaceutically acceptable excipients to form a mixture;
   b) wet-granulating the resulting mixture with a solution comprising surfactant;
   c) further mixing the obtained granulate with one or more further pharmaceutically acceptable excipients to form a further mixture, wherein the extragranular excipients comprises surfactant;
   d) compressing the mixture obtained in step c) into a tablet;
   and optionally
   e) coating the tablet.

12. The tablet composition according to claim 1, comprising 500 mg of abiraterone acetate.

13. The tablet composition according to claim 11, wherein said solution comprising a surfactant is an aqueous solution comprising a surfactant.

14. The tablet composition according to claim 1, wherein said granules further comprise (i) disintegrant intragranularly in an amount of from 1% to 8% by weight based on the total weight of the composition, (ii) binder intragranularly in an amount of from 1% to 5% by weight based on the total weight of the composition, and (iii) one or more diluents intragranularly in an amount of from 10% to 30% by weight based on the total weight of the composition.

15. The tablet composition according to claim 14, wherein said extragranular excipients further comprise (a) disintegrant in an amount from 1% to 8% by weight based on the total weight of the composition, and (b) a lubricant in a total amount of from 0.05% to 5% by weight based on the total weight of the composition.

16. The tablet composition according to claim 14, wherein said intragranular diluent is lactose monohydrate.

17. The tablet composition according to claim 16, wherein said binder is hypromellose.

18. The tablet composition according to claim 15, wherein the intragranular and extragranular surfactant is sodium lauryl sulphate.

19. The tablet composition according to claim 18, wherein said intragranular diluent is lactose monohydrate.

20. The tablet composition according to claim 19, wherein said binder is hypromellose.

* * * * *